United States Patent [19]

Greenshields

[11] Patent Number: 4,537,980

[45] Date of Patent: Aug. 27, 1985

[54] ACETALS

[75] Inventor: James N. Greenshields, Stockport, England

[73] Assignee: Imperial Chemical Industries Limited, London, England

[21] Appl. No.: 564,900

[22] Filed: Dec. 23, 1983

Related U.S. Application Data

[62] Division of Ser. No. 140,599, Apr. 15, 1980, Pat. No. 4,459,418.

[30] Foreign Application Priority Data

May 2, 1979 [GB] United Kingdom ................ 7915225

[51] Int. Cl.$^3$ .................. C07D 407/00; C07D 319/06; C07D 17/00
[52] U.S. Cl. .................................... 549/370; 549/374; 549/448; 549/453
[58] Field of Search ................ 549/374, 453, 370, 448

[56] References Cited

U.S. PATENT DOCUMENTS 2,095,814 10/1937 Hopff et al. .......................... 549/453
4,031,112 6/1977 Oppenlaender et al. ........... 549/374

FOREIGN PATENT DOCUMENTS 2020702 11/1979 United Kingdom ................ 549/453

Primary Examiner—Ethel G. Love
Attorney, Agent, or Firm—Cushman, Darby & Cushman

[57] ABSTRACT

A new method for the preparation of acetals of long chain fatty aliphatic aldehydes and polyols containing four or more hydroxyl groups which produces the acetals in a relatively pure form by reaction in a mutual solvent, preferably a $C_1$ to $C_4$ fatty carboxylic acid. The 'clean' acetals are useful emulsifying agents and their esters and polyalkoxy substituents are useful dispersants and surfactants for aqueous compositions.

4 Claims, No Drawings

ACETALS

CROSS REFERENCE TO RELATED APPLICATIONS

This application is a division of earlier application Ser. No. 140,599 filed Apr. 15, 1980, now U.S. Pat. No. 4,459,418 issued July 10, 1984.

This invention relates to a chemical process and more particularly to a process for the preparation of fatty acetals of polyhydric alcohols and to certain acetals and derivatives thereof.

Although it has been previously proposed, see for example U.S. Pat. No. 4,031,112, to prepare acetals by reaction of aldehydes with polyols the only specific examples of such reactions are with polyols containing less than 4 hydroxy groups except for the reaction between benzaldehydes and sorbitol (6 hydroxy groups). Although the above specification indicates that this reaction may also be performed with long-chain aliphatic aldehydes in place of benzaldehydes, it has now been found that, using the reaction conditions described in the above specification for the preparation of acetals of long-chain aldehydes the product and reactants undergo such extensive decomposition that the yield and quality of the product are commercially unacceptable.

According to the present invention there is provided a process for the preparation of an acetal which comprises reacting a polyol containing at least 4 hydroxyl groups with a fatty aliphatic aldehyde containing from 7 to 30 carbon atoms in a medium in which both reactants are at least partially soluble.

The reaction is particularly suitable with polyols containing at least 6 hydroxyl groups and especially with carbohydrates or products derived therefrom. Such polyols typically have from 6 to 5000 hydroxyl groups. A preferred group of polyols contains from 6 to 12 hydroxyl groups among which the hexitols are a specially preferred sub group.

Examples of such polyhydric alcohols are sorbitol, mannitol, glucose, sucrose, fructose, cellulose and starch. Other suitable polyhydric alcohols include partial ethers of starch and cellulose. These ethers include methyl ethers, hydroxypropylethers, hydroxymethylethers and carboxymethylethers. Although carbohydrate-derived polyols are preferred, others, for example partially hydrolysed polyvinyl acetate, polyvinyl alcohol and hydroxyl-containing alkyd resins, may also be used.

The aliphatic radical of the aldehyde is preferably an alkyl or alkenyl chain containing from 8 to 20 carbon atoms which may be straight or branched. Particularly useful aldehydes are those which are obtained by carbonylation of olefins and more particularly by carbonylation of α olefins.

Examples of suitable alkyl groups are those containing 7, 8, 9, 10, 11, 12, 13, 14, 15, 16 and 17 carbon atoms. A preferred aldehyde contains a mixture of $C_{12}$ and $C_{14}$ alkyl groups, particularly where each alkyl group comprises a mixture of straight and α-branched chains.

Suitable aldehydes for use in preparing acetals according to the present invention are conveniently prepared from olefines, especially α-olefins, by the "oxo" process, i.e. hydrocarbonylation of the double bonded carbon atoms. An especially preferred "oxo" aldehyde is a $C_{13}/C_{15}$ "oxo" aldehyde, prepared from mixed $C_{12}$ and $C_{14}$ α-olefines, comprising a 70:30 mixture of $C_{12}$ and $C_{14}$ alkyl chains approximately 50% of which are straight and 50% are branched.

A preferred group of solvents for the reaction medium are the $C_1-C_4$ fatty carboxylic acids, such as formic, propionic, butyric and especially acetic acid, and their halo-substituted derivatives.

Acetic acid is advantageous over other homologues because of its ready availability and cheapness.

The reaction is normally carried out by heating together the polyhydric alcohol and the fatty aldehyde in the solvent, preferably with the addition of a strong acid to catalyse acetal formation, under conditions such that the water formed in the reaction can be distilled out of the reaction mixture. The solvent can be recovered by fractional distillation and recycled.

It is not necessary to have sufficient solvent to ensure that a homogeneous solution is produced before the reaction commences provided at least a proportion of each reactant is in solution. It is preferred however that the reaction mixture is homogeneous by the end of the reaction period.

Any of those materials known in the art to catalyse acetal formation may be used in the process of this invention.

An example of a strong mineral acid catalyst which may be used is ortho phosphoric acid, preferably in the form of the commercially available aqueous solution of approximately 70% strength ("syrupy phosphoric acid"). An example of a strong organic acid is p-toluene sulphonic acid.

Termination of the reaction is conveniently monitored by examination of the reaction mixture using a suitable analytical technique such as gas-liquid chromatography (GLC). The final stages of the reaction may be carried out under sub-atmospheric pressure to assist in removing the last traces of water of reaction, thereby displacing the reaction in the direction of acetal formation, and to remove the solvent. Lower reaction temperatures can be used by conducting the reaction throughout at sub-atmospheric pressure.

When reaction has proceeded to the desired extent the reaction mixture may be cooled somewhat, for example to about 80° C. and the catalyst and any residual solvent neutralised by addition of a suitable base.

It is preferable to use the aldehyde to prepare the acetal in a direct manner, but if this does not react readily with the polyol, acetal formation can be promoted by first preparing a di-(lower alkyl)acetal, by reaction with a lower alkanol, followed by an acetal exchange reaction with the polyol under the above acetal reaction conditions.

It is preferred that the molar ratio of reactants is such as to leave no free aldehyde in the product at the end of the reaction. Any free hydroxyl groups in the product may be further reacted as hereinafter described. Where the polyol is a hexitol it is preferred to use from 1 to 3 moles of aldehyde per mole of polyol.

If the solvent is a fatty carboxylic acid some of the hydroxyl groups of the polyhydric alcohol may become esterified, so that the product can be a mixed acetal/ester, and such mixed acetal/esters constitute a further feature of the invention. Where it is desired to retain the ester groups it is preferred to use a weak base, or a strong base in an anhydrous form or as a dilute solution under mild conditions to neutralise any residual acidity in the product in order to avoid hydrolysis of the ester groups. However, if a product free from ester groups is desired, this may be achieved by selective hydrolysis of the ester groups preferably under strong alkaline conditions, the acetal groups being unaffected. This alkaline hydrolysis may be carried out, for example, by addition of a concentrated aqueous solution of a strong base such as sodium hydroxide, followed by a reaction period, optionally at above ambient temperature, for example 50°–250° and preferably 50°–150° C., to effect hydrolysis. The water may then subsequently be removed, for example, by distillation at or below atmospheric pressure. Distillation may be assisted by the addition of an azeotroping solvent. Alternatively the water may be removed by addition of a dehydration agent. If hydrolysis of the ester groups is required the previous neutralisation is not necessary because the strong base, in addition to hydrolysing any ester groups which may be present in the reaction product, also neutralises any residual acid in the product.

Finally, the reaction product may be freed from any solid contaminants by, for example, filtration of the warm product, for example through a bed of diatomaceous earth. Attempts to prepare acetals from polyhydric alcohols and fatty aldehydes by conventional methods, i.e. in the absence of a suitable reaction medium, result in the formation of dark-coloured and ill-defined products due to physical incompatibility of the reactants. The process of the present invention has the advantage that it provides products of good colour and well-defined structure.

Where the acetals or mixed acetal/esters obtained according to the process of the present invention contain free hydroxyl groups these may be reacted with one or more lower ($C_2$–$C_4$) alkylene oxides such as ethylene oxide or propylene oxide to give products containing polyoxyalkylene chains. When two different oxides are used, they may be employed in admixture, when the product will contain for example a random oxyethylene/oxypropylene copolymer chain or chains, or they may be reacted in any desired order to give a product containing a block copolymer chain or chains. Preferably the number of oxyalkylene groups introduced into the acetal is from 1 to 30.

The acetals prepared according to the process of the present invention, and their ester and polyoxyalkylene derivatives have useful surface active properties and can be used as surfactants, lubricants, emollients and surfactant intermediates. The acetals, acetal/esters and polyalkylene oxide derivatives prepared from $C_{13}/C_{15}$ oxoaldehydes and hexitols or higher polyols are particularly useful as surfactants because they combine good surface activity with good physical form. Acetals and their derivatives from higher aldehydes generally have inferior physical form while those from lower aldehydes have inferior surface activity. The acetals derived from the lower polyols eg hexitols may be used in the preparation of water in oil emulsions. Those derived from higher polyols and the alkoxylated derivatives may be used in aqueous pigment and agrochemical dispersions and emulsifiable composition and as lubricants.

The acetals based on linear hexitols, particularly hexitols derived from polysaccharides, such as sorbitol and mannitol, are produced in particularly high purity, as indicated by their pale colour, not achievable by other known processes and such acetals, having colours not exceeding 250 Hazen units, preferably less than 100 Hazen units constitute a further feature of the present invention. In the case of sorbitol based acetals colours not exceeding 50 Hazen units may be obtained.

The invention is illustrated by the following Examples in which parts and percentages are by weight unless otherwise stated, the ratio of parts by weight to parts by volume being that of the kilogram to the liter.

EXAMPLE 1

Sorbitol (70% aqueous syrup; 798 parts) is dried by stirring at 15 mm Hg pressure in a vessel fitted for distillation. The vacuum is released and glacial acetic acid (300 parts by volume), a mixed $C_{13}/C_{15}$ "oxo" aldehyde containing a 70:30 mixture of $C_{12}$ and $C_{14}$ alkyl chains in which 47% are linear and 53% are branched (80% of the branched chains having a α-methyl group) (1272 parts), and a 70% aqueous solution of phosphoric acid (3 parts) are added.

The mixture is heated to 125° C. with stirring. After 1 hour at 125° C., an aqueous distillate (220 parts by volume) together with an oil (6 parts by volume) have been collected and the reaction mixture is substantially homogeneous. GLC analysis shows that approximately 80% of the aldehyde has reacted.

After the mixture has been stirred at 125° C. for a further 2 hours a vacuum of 15 mm Hg is applied and heating is continued for a further 2.25 hours at 125° C. The product is then cooled to give 1776.5 parts of a substantially clear, very pale coloured viscous liquid. Residual catalyst is neutralised by stirring for 30 minutes at 80° C. with calcium hydroxide (20 parts), followed by filtration of the product through a bed of diatomaceous earth.

The neutralised, filtered product (1717.5 parts) is a clear liquid having the following properties:
Colour = <5 Hazen units
Viscosity at normal room temperature = ca. 6 poise
Equivalent weight by saponification value = 1020
Equivalent weight by hydroxyl value = 447
Free aldehyde <0.25% of original charge.

EXAMPLE 2

The procedure described in Example 1 is repeated except that the neutralisation with calcium hydroxide is omitted. At this stage the product is found to have a saponification value of 1170, expressed as an equivalent weight.

Sodium hydroxide solution (70° Tw; 153 parts by volume) is added to the product and the mixture is stirred at 80° C. for 1 hour. The water present is then removed by distillation under sub-atmospheric pressure, finally at 15 mm Hg. Solid is separated from the product by hot filtration through a filter bed of diatomaceous earth.

The product is a clear liquid having the following properties:
Colour = 20 Hazen units
Viscosity at normal room temperature = ca. 10 poise
Equivalent weight by saponification value = >20,000
Equivalent weight by hydroxyl value = 344
Free aldehyde <0.25% of original charge.

EXAMPLE 3

Sorbitol (70% aqueous syrup; 1596 parts) is dried as in Example 1. Glacial acetic acid (630 parts), an aldehyde as described in Example 1 (1395 parts) and phosphoric acid (6 parts by volume) are added.

The mixture is heated at 127° C. for 2½ hours with stirring in a vessel equipped for distillation with a dip-leg, through which is passed a slow stream of nitrogen. During this period 310 parts by volume of an acetic acid/water distillate and 6 parts by volume of an oil are collected and a maximum still head temperature of 100° C. is recorded.

The clear mixture is then stirred under 40 mm Hg vacuum at 127° C. for 2½ hours. A further 50 parts of glacial acetic acid is added and stirring under vacuum at 127° C. continued for a further 3½ hours.

The product is treated with calcium carbonate (37.6 parts), by stirring for 1 hour at 90° C. The product is then filtered under vacuum to give 2160 parts of a clear pale straw coloured viscous liquid.

Analysis for ester content gives the following result. Saponification value = 106.3 mg KOH/g.

From this result and the molar ratio of reactants used, the following average structural formula can be calculated:

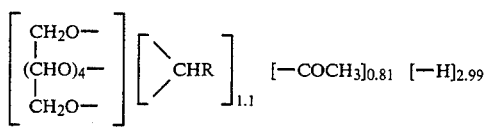

This structure has a theoretical hydroxyl value of 390 mg KOH/g which can be compared with a value of 324 mg KOH/g determined by analysis.

The product is soluble in ethanol and slightly soluble in toluene. Oil-in-water and water-in-oil emulsions of toluene can be prepared by suitable selection of phase ratios.

EXAMPLE 4

Sorbitol (70% aqueous syrup; 53.2 parts) is dried as in Example 1 in a reaction vessel equipped with a stirrer and then mixed with formic acid (30.5 parts), the aldehyde described in Example 1 (84.8 parts) and phosphoric acid (0.2 parts by volume). The temperature is then raised to 115° C., which causes distillation at a head temperature of 88° C. After 3½ hours on temperature 24 parts, by volume, of aqueous/acid distillate and 1 part by volume of an upper oil phase have distilled out. Analysis of the reaction mass by GLC shows that 78.2% of the original charge of aldehyde has reacted.

Reaction is continued for 2 hours at 18 mm Hg at 125° C. to increase the conversion of aldehyde to acetal and to remove residual formic acid. After cooling to 80° calcium carbonate (2.3 parts) is added and the mixture stirred for ½ hour at 80° C. over nitrogen. After filtering a clear pale straw coloured liquid (107.6 parts) is obtained.

Final analysis by GLC shows 96.2% of the original aldehyde charged is reacted.

A determined saponification value of 101.1 mg KOH/g is equivalent to 1.1 formate ester groups per molecule.

EXAMPLE 5

Example 4 is repeated replacing formic acid with propionic acid and using a reaction temperature of 140° C. with a corresponding distillation head temperature of 103° C.

After 1½ hours at 140° C., 95% of the original charge of aldehyde is found, by GLC, to have reacted. Residual propionic acid is removed by stirring for 2 hours at 146° C. under 15 mm Hg. After treatment with calcium carbonate and filtering as in Example 4, a pale straw liquid product somewhat more viscous than that prepared in Example 4, is obtained.

The determined saponification value of 60.6 mg KOH/g is consistent with 0.66 propionate ester groups per molecule.

EXAMPLE 6

A mixture of mannitol (182.2 parts) and glacial acetic acid (100 parts by volume) is heated at 80° C. in a vessel fitted with a stirrer and equipped for distillation to form a mobile paste. The aldehyde described in Example 1 (424 parts) and phosphoric acid (1 part by volume) are added and the temperature raised to 123° C. After 4 hours at 123° C. the pressure is reduced to about 15 mm and heating at 125° C. continued for a further 3½ hours. On cooling, the product (588.3 parts) is an off-white (colour = 70 Hazen units) thioxotropic paste.

This product can be used to prepare, for example, stable reverse water/xylene emulsions.

EXAMPLE 7

Sorbitol (70% aqueous syrup; 266 parts) is dried as described in Example 1. Glacial acetic acid (175 parts by volume), octanal (516 parts) and phosphoric acid (1 part by volume) are added and heated for 6 hours at 120° C. in a vessel equipped for distillation. The pressure is then reduced and residual acetic acid and some of the unreacted octanal are removed. After 10 hours at approximately 15 mm at 120° C. the product is cooled to room temperature. The final product is a very pale yellow liquid, insoluble in water and soluble in toluene. Unstable water/toluene emulsions can be made using this material.

The octanal used in this experiment is prepared from polymer gasoline heptene by hydroformylation (carbonylation).

EXAMPLE 8

Sorbitol (70% aqueous syrup; 266 parts) is dried as described in Example 1. The reaction vessel is then fitted with a Dean and Stark water separator. Nonanal (286 parts), glacial acetic acid (118 parts by volume) and phosphoric acid (1 part by volume) are added and the stirred reaction mixture heated to reflux temperature and held at this for 5 hours. The Dean and Stark separator is then replaced by a still head and distillation continued for 6½ hours at a maximum batch temperature of 139° C. A trace of an upper oily layer present in the distillate is returned to the reaction vessel and the product finally stripped for 2 hours at 120° C. at approximately 15 mm Hg using a slow nitrogen sponge.

The product is neutralised using sodium carbonate and filtered to give a pale yellow viscous liquid, which is insoluble in water.

The nonanal used in this preparation is prepared by hydroformylation (carbonylation) of commercially available diisobutylene.

EXAMPLE 9

A solution of sucrose (20.6 parts) in glacial acetic acid (300 parts by volume) is obtained by stirring the two components at 96°–99° C. under a nitrogen blanket for 1½ hours. The pale yellow slightly hazy solution is cooled to 50° C. and the aldehyde (14 parts) described in Example 1 and phosphoric acid (0.1 part by volume) are added.

The reaction mixture is heated at 50° C. and under a gradually decreasing pressure (from 120 mm Hg to 32 mm Hg) for 1 hour. At this stage the previously clear reaction mixture becomes turbid and a further quantity of glacial acetic acid (100 parts by volume) and phosphoric acid (0.5 parts by volume) are added to produce a clear solution. Reaction is continued for a further 19 hours with constant agitation at 50° C. and a final pressure of 10 mm Hg. During this period a further 10 parts of glacial acetic acid are added.

The product is then treated with 50 parts of 2N sodium hydroxide at 80° C. for 45 minutes. Sodium chloride (5 parts) is added to improve separation and the aqueous layer removed to leave a sticky viscous dark brown product. This material gives cloudy frothy solutions in water and stable water/toluene emulsions.

EXAMPLE 10

Sucrose (34.2 parts), aldehyde, as described in Example 1 (21.2 parts), glacial acetic acid (50 parts by volume) and p-toluene sulphonic acid monohydrate (0.5 part) are stirred under nitrogen in a reaction vessel equipped for vacuum distillation. After heating for 1¼ hours at 60° C. the pressure is lowered so that a steady distillation occurs at a head temperature of 32°-35° C. Distillation is continued under these conditions for 3¼ hours.

The product is at this stage a hazy orange coloured paste which is capable of stabilising toluene in water emulsions.

After washing with three portions of boiling water (200 parts×3) and drying over phosphorous pentoxide a clear viscous amber liquid is obtained. This final product is insoluble in water, soluble in toluene and gives water-in-oil emulsions of toluene.

EXAMPLE 11

A clear solution of glucose (54.1 parts) in glacial acetic acid (150 parts by volume) is produced by stirring for 15 minutes at 120° C. under a nitrogen blanket. An aldehyde (21.2 parts) as described in Example 1 and phosphoric acid (0.5 parts by volume) are added and the temperature increased to 130° C. over a period of 2 hours. During this time 116 parts by volume of distillate are collected. The pressure is then reduced to 20 mm Hg to complete the removal of acetic acid. After 70 minutes the vacuum is released and the product discharged and cooled.

The product is an amber solid, particularly soluble in water and toluene, soluble in isopropanol/water mixtures and stabilises emulsions of toluene in water.

EXAMPLE 12

A clear solution of a 1:1 molar condensation product of glucose and sorbitol (34.4 parts), prepared as described in U.S. Pat. No. 4,024,290, formic acid (17 parts by volume) and glacial acetic acid (17 parts by volume) is prepared by warming the stirred mixture under a blanket of nitrogen. An aldehyde as described in Example 1 (31.8 parts) and phosphoric acid (0.1 parts by volume) are added and the temperature increased to 125° C. During this heating period solvent mixture and water are removed by distillation. After 1½ hours a further 17 parts of glacial acetic acid are added and distillation continued for a further 1 hour at a batch temperature of 125° C. Residual solvents are then removed over a 1 hour period under 15 mm Hg.

The product is a pale yellow, cloudy, viscous liquid (68.5 parts). It is slightly soluble in water and can be used to stabilise reverse emulsions of toluene and water.

EXAMPLE 13

Dipentaerythritol (50.8 parts) and an aldehyde (84.8 parts) as described in Example 1 are condensed at 115° C. in a solution of glacial acetic acid (108 parts by volume) and formic acid (40 parts by volume) in a vessel fitted for distillation. After distilling for 4 hours at atmospheric pressure, vacuum is applied and distillation continued for 45 minutes at 20 mm Hg.

The product is neutralised by stirring with calcium carbonate (2.3 parts) for 30 minutes at 80° C. and then filtered.

The product is a pale straw coloured liquid, soluble in toluene and insoluble in water.

EXAMPLE 14

A product prepared as in Example 3 (660 parts) and potassium hydroxide (1.3 parts) are stirred in a pressure vessel and heated at 100° C. for 1 hour at 15 mm Hg with a slow nitrogen bleed through a dip-leg to remove any traces of water present. Ethylene oxide (690 parts) is then added over a period of 5½ hours, whilst maintaining the temperature at 130°-160° C. The product is then cooled to 100° C. and blown with nitrogen to remove any unreacted ethylene oxide.

The product (1320 parts) is a clear straw coloured liquid. Residual base catalyst is neutralised by adding 10 parts of water, blowing with carbon dioxide for 1 hour and filtering.

The hydroxyl value of the product is found to be 189 mg KOH/g, consistent with the addition of approximately ten ethoxylate groups per molecule of starting material.

EXAMPLE 15

Example 14 is repeated using 6 parts of potassium hydroxide and replacing ethylene oxide by propylene oxide (1366 parts). Reaction is carried out over 9 hours at 110°-120° C.

The product (1995 parts) is a clear liquid with a hydroxyl value of 121 mg KOH/g.

EXAMPLE 16

Dried sorbitol (18.2 parts) is dissolved at about 100° C. in glacial acetic acid (17 parts by volume). Phosphoric acid (0.1 parts by volume) and a mixed $C_{15}/C_{17}$ "oxo" aldehyde containing approximately 70% $C_{15}$ and 30% $C_{17}$ alkyl chains in which approximately 50% are branched and 50% are linear (48 parts) are then added.

The reaction is then continued using a technique similar to that described in Example 1.

The product is a straw coloured, clear, viscous liquid, insoluble in water which is capable of stabilising emulsions and reverse emulsions of toluene and water.

I claim:

1. An acetal having a color not exceeding 250 Hazen units derived from a polyol containing at least four hydroxyl groups and a fatty aliphatic aldehyde having an alkyl chain containing at least 11 and up to 20 carbon atoms.

2. An acetal according to claim 1 having a color not exceeding 100 Hazen units.

3. An acetal according to claim 1 in which the polyol containins at least six hydroxyl groups.

4. An acetal according to claim 1 in which the aldehyde is a mixed $C_{13}/C_{15}$ "oxo" aldehyde.

* * * * *